US00PP37789P2

(12) United States Plant Patent
Mukundan

(10) Patent No.: US PP37,789 P2
(45) Date of Patent: Oct. 20, 2026

(54) ***AGLAONEMA* PLANT NAMED 'MUKJUL'**

(50) Latin Name: *Aglaonema hybrida*
Varietal Denomination: MUKJUL

(71) Applicant: Parthasarathy Mukundan, Chennai (IN)

(72) Inventor: Parthasarathy Mukundan, Chennai (IN)

( * ) Notice: Subject to any disclaimer, the term of this patent is extended or adjusted under 35 U.S.C. 154(b) by 0 days.

(21) Appl. No.: 19/271,437

(22) Filed: Jul. 16, 2025

(51) Int. Cl.
*A01H 5/12* (2018.01)
*A01H 6/10* (2018.01)

(52) U.S. Cl.
USPC ..... Plt./376
CPC ..... *A01H 6/10* (2018.05)

(58) Field of Classification Search
USPC ..... Plt./376
See application file for complete search history.

(56) References Cited

U.S. PATENT DOCUMENTS

PP23,971 P2 * 10/2013 Mukundan ..... A01H 6/10
Plt./376

* cited by examiner

*Primary Examiner* — Susan Mccormick Ewoldt
*Assistant Examiner* — Zachariah Allan Kay
(74) *Attorney, Agent, or Firm* — C. Anne Whealy

(57) ABSTRACT

A new and distinct cultivar of *Aglaonema* plant named 'MUKJUL', characterized by its relatively compact; symmetrical and uniform shape; upright to outwardly arching plant habit; abundant sucker production and relatively short internodes gives a compact, dense and full plant form; upright to outwardly arching, glossy and narrowly elliptic leaves with acuminate apices; leaves are dark green in color with silvery green-colored splotches and chevrons; strong and flexible leaf petioles that are medium green in color; and relative tolerance to low production temperatures.

2 Drawing Sheets

Figure 1:
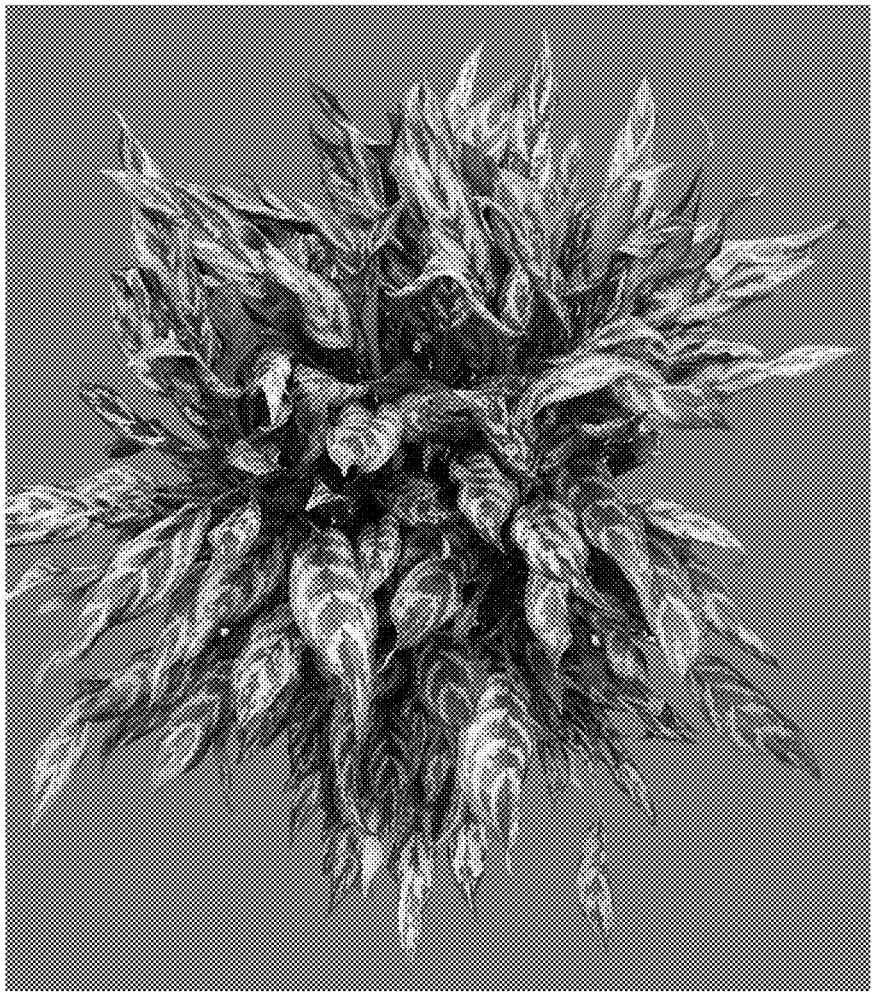

Botanical designation: *Aglaonema hybrida.*
Cultivar denomination: 'MUKJUL'.

BACKGROUND OF THE INVENTION

The present invention relates to a new and distinct cultivar of *Aglaonema* plant, botanically known as *Aglaonema hybrida* and hereinafter referred to by the name 'MUKJUL'.

The new *Aglaonema* plant is a naturally-occurring branch mutation of *Aglaonema hybrida* 'Juliet', not patented. The new *Aglaonema* plant was discovered and selected by the Inventor in October, 2017 on a single plant from within a population of plants of 'Juliet' in a controlled greenhouse environment in Chennai, India.

Asexual reproduction of the new *Aglaonema* plant by cuttings and divisions in a controlled environment in Chennai, India since October, 2018 has shown that the unique features of this new *Aglaonema* plant are stable and reproduced true to type in successive generations of asexual reproduction.

SUMMARY OF THE INVENTION

Plants of the new *Aglaonema* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'MUKJUL'. These characteristics in combination distinguish 'MUKJUL' as a new and distinct *Aglaonema* plant:

1. Relatively compact; symmetrical and uniform shape; upright to outwardly arching plant habit.
2. Abundant sucker production and relatively short internodes gives a compact, dense and full plant form.
3. Upright to outwardly arching, glossy and narrowly elliptic leaves with acuminate apices; leaves are dark green in color with silvery green-colored splotches and chevrons.
4. Strong and flexible leaf petioles that are medium green in color.
5. Relatively tolerant to low production temperatures.

Plants of the new *Aglaonema* differ primarily from plants of the mutation parent, 'Juliet', in the following characteristics:

1. Plants of the new *Aglaonema* are larger, more symmetrically uniform, more vigorous and faster-growing than plants of 'Juliet'.
2. Plants of the new *Aglaonema* produce more suckers per plant and are denser and bushier than plants of 'Juliet'.
3. Leaves of plants of the new *Aglaonema* are longer and broader than leaves of 'Juliet'.
4. Leaf petioles of plants of the new *Aglaonema* are longer than leaf petioles of plants of 'Juliet'.

Plants of the new *Aglaonema* can be compared to plants of *Aglaonema hybrida* 'Mukgres', disclosed in U.S. Plant Pat. No. 23,971. In side-by-side comparisons, plants of the new *Aglaonema* differ primarily from plants of 'Mukgres', in the following characteristics:

1. Leaves of plants of the new *Aglaonema* are longer and narrower with more undulating margins than leaves of 'Mukgres'.

2. Leaves of plants of the new *Aglaonema* are dark green in color with silvery green-colored splotches and chevrons whereas leaves of plants of 'Mukgres' have dark green- colored midveins, margins and irregular chevrons alternating with contrasting greyed green-colored irregular chevrons.
3. Leaf petioles of plants of the new *Aglaonema* are longer and lighter green in color than leaf petioles of plants of 'Mukgres'.

BRIEF DESCRIPTION OF THE PHOTOGRAPHS

The accompanying photographs illustrate the overall appearance of the new *Aglaonema* plant showing the colors as true as it is reasonably possible to obtain in colored reproductions of this type. Colors in the photographs may differ slightly from the color values cited in the detailed botanical description which accurately describe the colors of the new *Aglaonema* plant.

The photograph on the first sheet (FIG. 1) is a side perspective view of a typical plant of 'MUKJUL' grown in a container.

Figure 2:
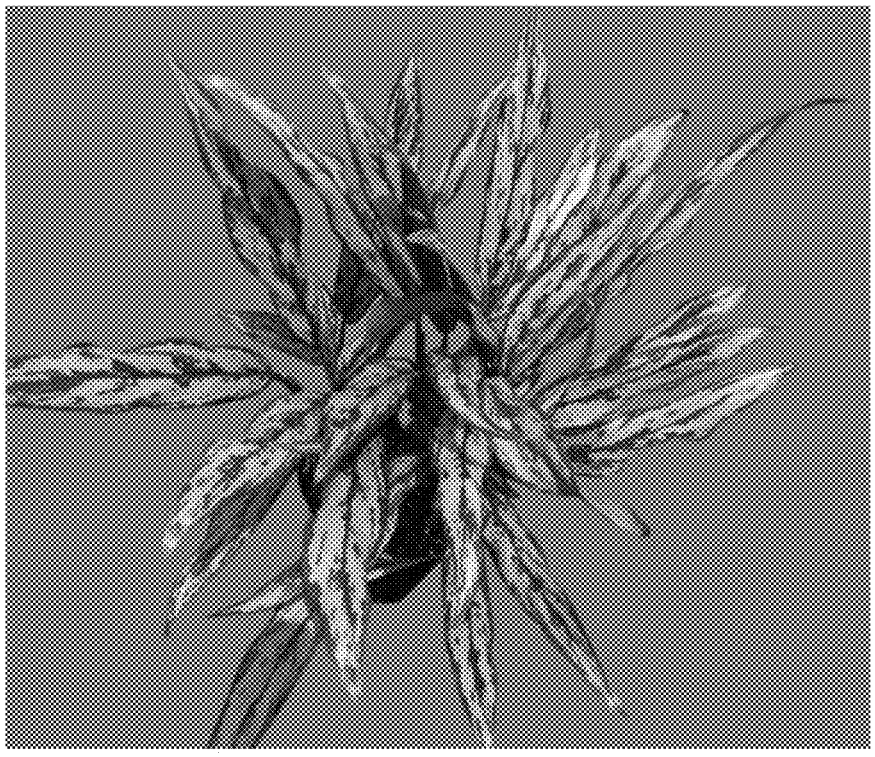

The photograph on the second sheet (FIG. 2) is a side perspective view of a typical plant of the mutation parent, 'Juliet', grown in a container.

DETAILED BOTANICAL DESCRIPTION

The aforementioned photographs and following observations and measurements describe plants grown in 15-cm containers during the early spring and summer in a polypropylene shade cloth-covered greenhouse in Miami, Florida. Plants were grown under environmental conditions and cultural practices which approximate those generally used in commercial *Aglaonema* production. During the production of the plants, temperatures ranged from 10° C. to 38° C. Plants were one year old when the photographs and the detailed description were taken. In the following description, color references are made to The Royal Horticultural Society Colour Chart, 2015 Edition, except where general terms of ordinary dictionary significance are used.

Botanical classification: *Aglaonema hybrida* 'MUKJUL'.

Parentage: Naturally-occurring branch mutation of *Aglaonema hybrida* 'Juliet', not patented.

Propagation:

*Type*.—By top cuttings, stem cuttings and divisions.

*Time to initiate roots, summer*.—About three to four weeks at temperatures about 25° C. to 32° C.

*Time to initiate roots, winter*.—About 30 to 40 days at temperatures about 12° C. to 25° C.

*Time to produce a rooted young plant, summer*.—About 30 to 35 days at temperatures about 25° C. to 32° C.

*Time to produce a rooted young plant roots, winter*.—About 45 to 60 days at temperatures about 12° C. to 25° C.

*Root description*.—Medium in thickness, fleshy; typically off-white in color, actual color of the roots dependent on substrate composition, water quality, fertilizer, substrate temperature and age of roots.

*Rooting habit*.—Freely branching; profusely dense.

Plant description:

*Plant and growth habit*.—Relatively compact; symmetrical and uniform shape; upright to outwardly arching plant habit; moderately vigorous with a large number of suckers produced; abundant sucker production and relatively short internodes gives a compact, dense and full plant form; leaves held upright to outwardly arching on strong petioles.

*Plant height, from soil level to top of leaf plane*.—About 45 cm.

*Plant diameter or spread*.—About 62.5 cm.

*Stem description*.—Aspect: Upright. Strength: Strong, sturdy; slightly flexible. Diameter, at the base: About 1.25 cm to 1.5 cm. Internode length, at the base: About 9 mm to 11 mm. Texture and luster: Smooth, glabrous; semi-glossy. Color: Developing: Close to 144A. Developed: Close to between 146A and 147A.

Leaf description:

*Arrangement*.—Whorled; simple.

*Length*.—About 21 cm.

*Width*.—About 4.35 cm.

*Shape*.—Narrowly elliptic.

*Apex*.—Acuminate.

*Base*.—Cuneate with obtuse tendencies.

*Margin*.—Entire; undulate.

*Texture and luster, upper surface*.—Smooth, glabrous; glossy.

*Texture and luster, lower surface*.—Smooth, glabrous; slightly glossy.

*Venation pattern*.—Pinnate.

*Color*.—Developing leaves, upper surface: Ground color, close to 146A; splotches and chevrons, close to N148A, N148B and 191A to 191B. Developing leaves, lower surface: Close to 146A. Fully expanded leaves, upper surface: Ground color, close to N189A, 147A and N137A; splotches and chevrons, close to N148A, N148B and 191A to 191B; venation, similar to lamina colors. Fully expanded leaves, lower surface: Close to 146A; venation, close to 146A.

*Petioles*.—Aspect: Initially, erect to outwardly arching with development. Length: About 15 cm. Diameter, distally: About 4 mm by 5 mm. Diameter, proximally: About 9 mm by 12 mm. Strength: Strong, flexible; not brittle. Texture and luster: Smooth, glabrous; semi-glossy. Color: Outer surface: Close to 146A. Inner surface: Close to 145D. Wing length: About 10.75 cm. Wing diameter, proximally: About 5 mm. Wing texture: Smooth, glabrous; towards the margin, membranous. Wing color: Outer surface: Close to 146A. Inner surface: Close to 154D.

Inflorescence description: To date, inflorescence development has not been observed on plants of the new *Aglaonema*.

Pathogen & pest resistance: To date, plants of the new *Aglaonema* have not been observed to be resistant to pathogens or pests common to *Aglaonema*.

Temperature tolerance: Plants of the new *Aglaonema* have been observed to be relatively low temperature tolerant and to tolerate temperatures ranging from about 10° C. to about 38° C.

It is claimed:

1. A new and distinct *Aglaonema* plant named 'MUKJUL' as herein illustrated and described.

* * * * *